United States Patent [19]

Gorbach

[11] Patent Number: 6,060,070
[45] Date of Patent: May 9, 2000

[54] ISOFLAVONOIDS FOR TREATMENT AND PREVENTION OF AGING SKIN AND WRINKLES

[76] Inventor: Sherwood L. Gorbach, 31 Perry La., Weston, Mass. 02193

[21] Appl. No.: 08/873,314

[22] Filed: Jun. 11, 1997

[51] Int. Cl.[7] .............................. A61K 7/00; A61K 31/35
[52] U.S. Cl. ....................... 424/401; 424/439; 424/440; 424/441; 424/195.1; 514/456
[58] Field of Search ............... 514/456; 424/47, 424/439, 440, 441, 195.1

[56] References Cited

U.S. PATENT DOCUMENTS

| | | | |
|---|---|---|---|
| 4,218,489 | 8/1980 | Zilliken | 426/545 |
| 5,516,528 | 5/1996 | Hughes et al. | 424/464 |
| 5,539,129 | 7/1996 | Zysman | 549/430 |
| 5,603,936 | 2/1997 | Monte | 424/195.1 |
| 5,654,011 | 8/1997 | Jackson et al. | 424/635 |
| B1 5,498,631 | 3/1998 | Gorbach et al. | 514/456 |

FOREIGN PATENT DOCUMENTS 60-61513  4/1985  Japan.

*Primary Examiner*—Thurman K. Page
*Assistant Examiner*—Lakshmi Channavajjala
*Attorney, Agent, or Firm*—Clark & Elbing LLP

[57] ABSTRACT

A method of treating or preventing, in a person, one or more symptoms of aging skin, said method comprising topically administering to the skin of said person a composition comprising one or more isoflavonoids selected from the group consisting of genistein, daidzein, biochanin A, formononetin, O-desmethylangolensin, glycitin, and equol, in a topically acceptable base, wherein the isoflavonoid concentration is between 1 and 40 mg per gram of base.

13 Claims, No Drawings

ISOFLAVONOIDS FOR TREATMENT AND PREVENTION OF AGING SKIN AND WRINKLES

BACKGROUND OF THE INVENTION

The present invention relates to therapies for the prevention and treatment of aging skin and wrinkles.

It has long been recognized that as people grow older, significant changes occur in their skin, specifically thinning, deepening of facial creases (wrinkling), and increased extensibility and flaccidity. These changes are related to reduced skin tonicity and diminished skin hydration. The underlying causes for these changes are believed to be lowered collagen content and reduced number of elastic fibers in the skin. Estrogen hormones have been used for treating aging skin either in an oral form or as topical skin creams or gels. These treatments have produced augmented skin thickness, greater hydration, and improvements in elasticity and firmness. It is believed that the effectiveness of estrogen hormones is related to the increase in the amount of skin collagen which is caused by stimulating collagen synthesis. Besides being able to demonstrate the increase in collagen content after estrogen treatment, there is also an increase in collagen and elastic fibers, which improve the mechanical properties of skin. While estrogen can be used for treating and preventing aging skin, potential users of this hormone are concerned about the risk of side effects, particularly the increased risk of cancers of the breast and uterus. In addition, estrogen typically is not used in men, who also have problems with aging skin and wrinkles, because of the undesirable side effects of this female hormone in male users. Safer and effective therapies for treating and preventing aging skin and wrinkles in both women and men continue to be sought.

SUMMARY OF THE INVENTION

The invention features the topical use of purified isoflavonoids, which are constituents of soy beans and other plants such as clover, to effectively treat and prevent symptoms of aging skin, such as wrinkles. Without being bound by any theory, it is believed that isoflavonoids have significant estrogenic activity, acting in the skin by stimulating the synthesis of collagen. These compounds are safe and cause no significant side-effects. Purified isoflavonoids which may be administered according to the invention include genistein, daidzein, biochanin A, formononetin, O-desmethylangolensin, glycitin, and equol; these may be administered alone or in combination.

Accordingly, the invention provides a method of treating or preventing, in a person, one or more symptoms of aging skin, e.g., wrinkles, by applying to the person's skin a composition containing a dermatologically acceptable base containing between 1 and 40 mg purified isoflavonoid per gram of base; the isoflavonoid is one of the naturally-occurring isoflavonoids listed above.

By "purified" is meant the isoflavonoid is in a form which is more concentrated than the form in which it occurs naturally in plants.

Preferred topical formulations are creams, ointments, lotions, emollient creams and ointments, moisturizing lotions, and gels. The purified isoflavonoids can also be included in a transdermal delivery system or patch.

The purified isoflavonoids of the invention can also be included in cosmetics (e.g., makeup); preferred forms are lotions, creams, moisturizing creams and lotions, skin oils, skin sprays, and gels.

Preferably, the topical composition containing the purified isoflavonoids is applied to the skin once or twice per day.

Alternatively, the invention features a method for treating or preventing one or more symptoms of aging skin in a male person or a female person three or more years past the onset of menopause, by administering (preferably orally) to the person a composition containing one or more purified isoflavonoids selected from the group consisting of genistein, daidzein, biochanin A, formononetin, O-desmethylangolensin, glycitin, and equol, in an amount sufficient to produce a transient concentration of the bloodstream of the person of at least 50 nm/l. Preferably, the composition is administered orally, providing a dosage of at least 20 mg of total isoflavonoid per serving. The orally-administerable composition can be a non-naturally occurring dietary product such as a convectionary bar, cereal, biscuit, or beverage. Alternatively, the composition can take the form of a medicament such as a pill, capsule, tablet, powder, or syrup, in which the total isoflavonoid is present in at least an amount of 20 mg per unit dose. Preferably, the composition provides a dosage of at least 20 mg of total isoflavonoid per serving. The orally-administerable composition can be a non-naturally occurring dietary product such as a convectionary bar, cereal, biscuit, or beverage. Alternatively, the composition can take the form of a medicament such as a pill, capsule, tablet, powder, or syrup, in which the total isoflavonoid is present in at least an amount of 20 mg per unit dose. Preferably, the dietary product or medicament is orally consumed by the person once, twice, or three times per day, to provide a daily oral isoflavonoid dose of between 20 and 300 mg. Preferably, the oral ingestion of the composition is sufficient to produce a transient concentration in the bloodstream of the person of at least 50 nm of total isoflavonoid per liter of blood. By "purified" isoflavonoid is meant an isoflavonoid in more concentrated form than occurs in plants.

Other features and advantages of the invention will be apparent from the Detailed Description thereof, and from the claims.

DETAILED DESCRIPTION

Isoflavonoids are naturally occurring compounds, found primarily in soy beans. These compounds are also found in high concentrations in red clover and in lower amounts in many other types of plants. An isoflavonoid-containing fraction (containing purified isoflavonoids) useful in the invention can be extracted from a soy or plant product using known methods. It is preferred that the isoflavonoids be extracted and concentrated from soy beans or soy powder, but other plants such as clover can be used. Isoflavonoids are also available commercially in substantially pure form.

The purified isoflavonoid, in the dermatologically acceptable base, is applied directly to the skin surface. The topical composition should be left on the skin for a sufficient period of time to allow the isoflavonoid to be substantially absorbed into the skin and the capillaries supplying the skin; generally, this period of time should be at least one, and preferably at least three hours. Where the topical composition is a cosmetic, it can be removed in the manner of ordinary cosmetics, e.g., using "cold cream." Because the isoflavonoids are not toxic, the topical composition can be applied at bedtime and left on the face, or other skin surface, overnight.

The isoflavonoid-containing composition can also be included in a transdermal delivery system or patch. The transdermal patch can be of conventional form, e.g., that used to deliver sustained doses of nicotine or estrogen.

Isoflavonoids have similar chemical properties to estrogens, e.g., they are poorly soluble in water but are readily soluble in alcohols and other organic solvents. For topical applications, either as a medicament or incorporated into a cosmetic, isoflavonoid is mixed in a base with ingredients such as alcohol, mineral oil, glyceryl monostearate, ether complex of fatty acids, cetyl alcohol, lanolin, propylene glycol, stearyl alcohol, and sodium lauryl sulfate. The concentration of isoflavonoid is 1 to 40 mg per gram of the base, more preferably 10–25 mg per gram of base.

Other embodiments are within the claims.

I claim:

1. A method of treating or preventing one or more symptoms of aging skin in a male human, or in a female human who is three or more years past the onset of menopause, said method comprising administering to the person a composition comprising one or more purified isoflavonoids selected from the group consisting of genistein, daidzein, biochanin A, formononetin, O-desmethylangolensin, glycitin, and equol, in an amount sufficient to produce a transient concentration at least 50 nanomoles/liter of said isoflavonoids in the bloodstream of said person.

2. The method of claim 1, wherein said composition is administered orally, in a dosage of at least 20 mg of isoflavonoid per serving.

3. The method of claim 2, wherein said composition is administered once, twice, or three times per day.

4. The method of claim 1, wherein said composition is in the form of a non-naturally occurring dietary product.

5. The method of claim 4, wherein said isoflavonoid contains at least 20 mg/serving of said isoflavonoid.

6. The method of claim 4, wherein said dietary product is a confectionary bar.

7. The method of claim 4, wherein said dietary product is a cereal.

8. The method of claim 4, wherein said dietary product is a biscuit.

9. The method of claim 4, wherein said dietary product is a beverage.

10. The method of claim 1, wherein said composition is in the form of a medicament.

11. The method of claim 10, wherein said composition contains at least 20 mg/unit dose of isoflavonoid.

12. The method of claim 10, wherein said medicament is in the form of a pill, capsule, tablet, powder, or syrup.

13. The method of claim 10, wherein said medicament is consumed orally by said patient once, twice, or three times a day.

* * * * *